(12) United States Patent
Jaramillo

(10) Patent No.: US 9,321,922 B2
(45) Date of Patent: Apr. 26, 2016

(54) COMPOSITION AND METHOD FOR REDUCING BACTERIAL BIOFILM FORMATION IN CONNECTION WITH A DENTAL PROCEDURE

(71) Applicant: LOMA LINDA UNIVERSITY, Loma Linda, CA (US)

(72) Inventor: David E. Jaramillo, Loma Linda, CA (US)

(*) Notice: Subject to any disclaimer, the term of this patent is extended or adjusted under 35 U.S.C. 154(b) by 0 days.

(21) Appl. No.: 14/364,072

(22) PCT Filed: Dec. 10, 2012

(86) PCT No.: PCT/US2012/068806
§ 371 (c)(1),
(2) Date: Jun. 9, 2014

(87) PCT Pub. No.: WO2013/090204
PCT Pub. Date: Jun. 20, 2013

(65) Prior Publication Data
US 2014/0366772 A1 Dec. 18, 2014

Related U.S. Application Data

(60) Provisional application No. 61/569,692, filed on Dec. 12, 2011.

(51) Int. Cl.
| | | |
|---|---|---|
| A61K 6/00 | (2006.01) |
| C09D 5/14 | (2006.01) |
| C09D 5/16 | (2006.01) |
| C08K 5/05 | (2006.01) |
| C08K 5/092 | (2006.01) |

(52) U.S. Cl.
CPC .......... C09D 5/1625 (2013.01); A61K 6/0035 (2013.01); A61K 6/0038 (2013.01); A61K 6/0067 (2013.01); C08K 5/05 (2013.01); C08K 5/092 (2013.01)

(58) Field of Classification Search
CPC . A61K 6/0035; A61K 6/0038; A61K 6/0067; C09D 5/1625; C09D 5/14; C08K 5/05; C08K 5/092
USPC ....................................................... 106/15.05
See application file for complete search history.

(56) References Cited

U.S. PATENT DOCUMENTS

| | | | |
|---|---|---|---|
| 6,071,528 A | 6/2000 | Jensen | |
| 6,303,557 B1 * | 10/2001 | Colclough | 510/382 |
| 2002/0162800 A1 * | 11/2002 | Back et al. | 210/698 |
| 2003/0161758 A1 * | 8/2003 | Whiteley | 422/28 |
| 2005/0061357 A1 * | 3/2005 | Steward et al. | 134/6 |
| 2006/0205838 A1 | 9/2006 | Velamakanni et al. | |
| 2009/0186079 A1 | 7/2009 | Nichols et al. | |
| 2010/0278906 A1 * | 11/2010 | Sondgeroth et al. | 424/450 |
| 2010/0285148 A1 | 11/2010 | Wlaschin et al. | |
| 2011/0104644 A1 | 5/2011 | Primus et al. | |

FOREIGN PATENT DOCUMENTS

WO   WO 2009/125305 A2 * 10/2009 ............... C11D 3/24

OTHER PUBLICATIONS

Loma Linda University, International Search Report and Written Opinion of the International Searching Authority issued in the parent International Patent Application PCT/US2012/068806 on Feb. 22, 2013.
Loma Linda University, International Preliminary Report on Patentability issued in the parent International Patent Application PCT/US2012/068806 on Nov. 29, 2013.

* cited by examiner

Primary Examiner — Anthony J Green
(74) Attorney, Agent, or Firm — Knobbe, Martens, Olson & Bear, LLP

(57) ABSTRACT

A composition for reducing bacterial biofilm formation after endodontic therapy comprising water, ethanol, benzalkonium chloride, citric acid, and nonionic surfactant. A method of making a composition for reducing bacterial biofilm. A method for reducing bacterial biofilm formation after a dental procedure.

24 Claims, 4 Drawing Sheets

COMPOSITION AND METHOD FOR REDUCING BACTERIAL BIOFILM FORMATION IN CONNECTION WITH A DENTAL PROCEDURE

CROSS-REFERENCE TO RELATED APPLICATIONS

The present Application is a national stage of International Patent Application No. PCT/US2012/068806 titled "Composition and Method for Reducing Bacterial Biofilm Formation in Connection With a Dental Procedure," which claims the benefit of U.S. Provisional Patent Application No. 61/569,692 entitled "Composition and Method for Reducing Bacterial Biofilm Formation after Endodontic Therapy," filed Dec. 12, 2011, the contents of which are incorporated in this disclosure by reference in their entirety.

BACKGROUND

Endodontic therapy generally involves removal of the pulp of a tooth to eliminate an active infection, and the filling of the root canal space created by the endodontic therapy to prevent future infection. Endodontic therapy failure is generally due to persistent infection within the root canal space where bacteria form biofilms of microbial communities that adhere to dentinal tubules, root canal walls or external apical surfaces or a combination of these. In many cases, these persistent infections originate by re-colonization of bacteria through coronal leakage. The root canal environment, especially in areas difficult to reach by mechanical cleaning, provides a variety of conditions which favor the formation of biofilms, such as for example the presence of moisture, suitable attachment surfaces and nutrient sources from exudates of the periapical tissues. Bacterial biofilm communities are encased in an extracellular polymeric matrix that makes biofilms inherently resistant to antibacterial agents due to physical diffusion barriers and physiological differences between the biofilm communities and the host. For example, a recent in vitro study showed that wild-strain bacteria of endodontic origin grown over 8 days on dentin slices of extracted teeth generate biofilms that were resistant to eradication by ampicillin, azithromycin, clindamycin, doxycycline and metronidazole.

Therefore, several strategies have been used to decrease the formation of biofilms to levels below a threshold of interference with endodontic therapy. One strategy has been to increase the physical removal of bacteria during endodontic therapy. Other strategies have been to inhibit the growth of bacteria and to reduce secondary colonization of the root canal, including treating surfaces with different repelling substances, incorporating antimicrobial products into surface materials, coating surfaces with antimicrobials, and by modifying the physicochemical properties of the surfaces to make the surfaces less favorable to biofilm formation. Thus far, however, these techniques have not been sufficiently successful to prevent or control the formation of biofilms in root canals.

Therefore, there is a need for a method for reducing bacterial biofilm formation after endodontic therapy.

SUMMARY

According to one embodiment of the present invention, there is provided a composition for reducing bacterial biofilm formation in connection with a dental procedure. The composition comprises a) water; b) an alcohol; c) a biocide; d) a chelating agent; and e) a surfactant. In one embodiment, the water is distilled water. In another embodiment, the composition comprises between 30% and 80% water. In another embodiment, the composition comprises between 50% and 70% water. In another embodiment, the composition comprises 60% water. In another embodiment, the alcohol is ethanol. In another embodiment, the composition comprises between 15% and 40% ethanol. In another embodiment, the composition comprises between 17% and 30% ethanol. In another embodiment, the composition comprises 20% ethanol. In another embodiment, the biocide is benzalkonium chloride. In another embodiment, the composition comprises between 5% and 20% benzalkonium chloride. In another embodiment, the composition comprises between 10% and 15% benzalkonium chloride. In another embodiment, the composition comprises 12% benzalkonium chloride. In another embodiment, the chelating agent is citric acid. In another embodiment, the composition comprises between 2% and 8% citric acid. In another embodiment, the composition comprises between 4% and 6% citric acid. In another embodiment, the composition comprises 5% citric acid. In another embodiment, the surfactant is a nonionic surfactant. In another embodiment, the nonionic surfactant is Triton X-100. In another embodiment, the nonionic surfactant is Triton X-100, where the composition comprises between 0.05% and 0.2% Triton X-100. In another embodiment, the nonionic surfactant is Triton X-100, where the composition comprises between 0.08% and 0.15% Triton X-100. In another embodiment, the nonionic surfactant is Triton X-100, where the composition comprises 0.1% Triton X-100. In a preferred embodiment, the composition comprises by weight: a) 50-67% water, b) 17.5-30% ethanol, c) 11-14% benzalkonium chloride, d) 4-5% citric acid, and e) 0.09 to 0.11% Triton X-100.

According to another embodiment of the present invention, there is provided a method of making a composition for reducing bacterial biofilm according to the present invention, the method comprising combining the water, the alcohol, the biocide, the chelating agent, and the surfactant.

According to another embodiment of the present invention, there is provided a method for reducing bacterial biofilm formation in connection with a dental procedure, where the method comprises providing a composition according to the present invention. In one embodiment, the dental procedure is selected from the group consisting of an endodontic procedure, preparation for placement of a restorative material, and preparation for placement of a dental crown.

DRAWINGS

These and other features, aspects and advantages of the present invention will become better understood with regard to the following description, appended claims, and accompanying drawings where:

DESCRIPTION

Figure 1:
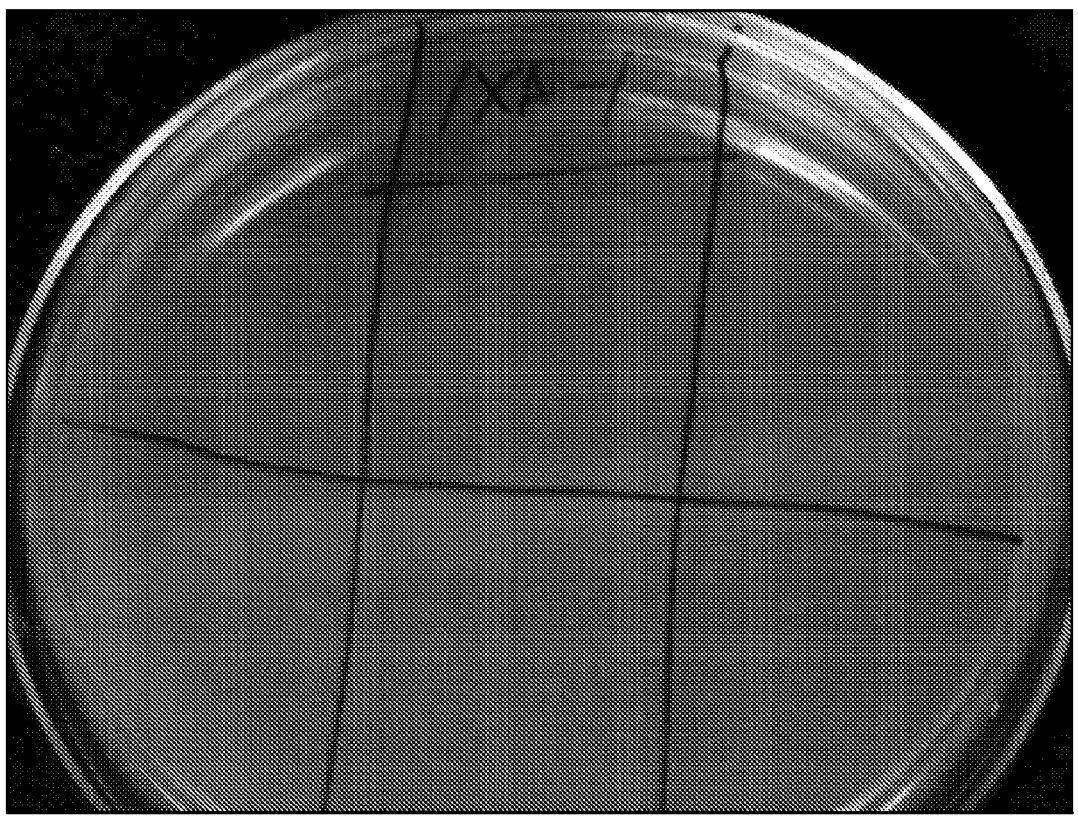
FIG. 1 is a photograph of an agar plate where the test sample was treated with a composition according to the present invention, demonstrating that no bacterial growth is visible.

According to one embodiment of the present invention, there is provided a composition for reducing bacterial biofilm formation in connection with a dental procedure. In one embodiment, the dental procedure is selected from the group consisting of an endodontic procedure such as a root canal, preparation for placement of a restorative material, and preparation for placement of a dental crown. According to another embodiment of the present invention, there is provided a method of making a composition for reducing bacterial biofilm, where the composition is a composition according to the present invention. According to another embodiment of the present invention, there is provided a method for reducing bacterial biofilm formation in connection with a dental procedure, where the method comprises providing a composition according to the present invention. In one embodiment, the dental procedure is selected from the group consisting of an endodontic procedure such as a root canal, preparation for placement of a restorative material, and preparation for placement of a dental crown. The composition and the methods will now be disclosed in detail.

As used in this disclosure, except where the context requires otherwise, the term "comprise" and variations of the term, such as "comprising," "comprises" and "comprised" are not intended to exclude other additives, components, integers or steps.

As used in this disclosure, except where the context requires otherwise, the method steps disclosed are not intended to be limiting nor are they intended to indicate that each step is essential to the method or that each step must occur in the order disclosed.

Except as indicated otherwise, all percents for components of the composition according to the present invention are expressed in weight percents.

According to one embodiment of the present invention, there is provided a composition for reducing bacterial biofilm formation in connection with a dental procedure. In one embodiment, the dental procedure is selected from the group consisting of an endodontic procedure such as a root canal, preparation for placement of a restorative material, and preparation for placement of a dental crown. The composition comprises a) water, b) an alcohol, c) a biocide, d) a chelating agent, and e) a surfactant. Any suitable substance can be used for each of these five components, as will be understood by those with skill in the art with reference to this disclosure. In one embodiment, the composition is in the form of a liquid. In another embodiment, the composition is in the form of a gel.

The composition of the present invention comprises water. In a preferred embodiment, the water is distilled water. Water has a liquid density of 1.0 g/ml. In one embodiment, the composition comprises between 30% and 80% water. In a preferred embodiment, the composition comprises between 50% and 70% water. In a particularly preferred embodiment, the composition comprises 60% water.

The composition of the present invention further comprises an alcohol. In one embodiment, the alcohol is ethanol. Ethanol has a liquid density of about 0.789 g/ml. In one embodiment, the composition comprises between 15% and 40% ethanol. In a preferred embodiment, the composition comprises between 17% and 30% ethanol. In a particularly preferred embodiment, the composition comprises 20% ethanol.

The composition of the present invention further comprises a biocide. In one embodiment, the biocide is benzalkonium chloride (also known as alkyldimethylbenzylammonium chloride and ADBAC). Benzalkonium chloride has a specific gravity of about 0.98 g/ml. In one embodiment, the composition comprises between 5% and 20% benzalkonium chloride. In a preferred embodiment, the composition comprises between 10% and 15% benzalkonium chloride. In a particularly preferred embodiment, the composition comprises 12% benzalkonium chloride.

The composition of the present invention further comprises a chelating agent. In one embodiment, the chelating agent is citric acid (2-hydroxypropane-1,2,3-tricarboxylic acid). In one embodiment, the composition comprises between 2% and 8% citric acid. In a preferred embodiment, the composition comprises between 4% and 6% citric acid. In a particularly preferred embodiment, the composition comprises 5% citric acid.

The composition of the present invention further comprises a surfactant. In one embodiment, the surfactant is a nonionic surfactant. In a preferred embodiment, the nonionic surfactant is Triton X-100, $(C14H22O(C2H4O)n)$. Triton X-100 has a specific gravity of about 1.07 g/ml. In one embodiment, the composition comprises between 0.05% and 0.2% Triton X-100. In a preferred embodiment, the composition comprises between 0.08% and 0.15% Triton X-100. In a particularly preferred embodiment, the composition comprises 0.1% Triton X-100.

In a preferred embodiment, the composition comprises by weight: a) 50-67% water, b) 17.5-30% ethanol, c) 11-14% benzalkonium chloride, d) 4-5% citric acid, and e) 0.09 to 0.11% Triton X-100.

According to another embodiment of the present invention, there is provided a method of making a composition for reducing bacterial biofilm, where the composition is a composition according to the present invention. The method comprises combining the water, the alcohol, the biocide, the chelating agent, and the surfactant. In one embodiment, the method comprises, first, providing a 50%:50% by volume mixture of water/ethanol. In one embodiment, the method comprises combining 50 ml of distilled water with 50 ml of ethanol to produce 100 ml. In another embodiment, the method comprises, first, providing a 30%:70% by volume mixture of water/ethanol. In one embodiment, the method comprises combining 30 ml of distilled water with 70 ml of ethanol to produce 100 ml. Next, the method comprises taking 50 ml of the 50%:50% by volume mixture or 50 ml of the 30%:70% by volume mixture, and adding 30 ml of distilled water. This mixture is then stirred using a magnetic stirrer. Then, the method comprises adding either 13 g of powdered benzalkonium chloride or 13 ml of liquid benzalkonium chloride to the mixture, and stirring the mixture until the benzalkonium chloride is completed dissolved. Next, the method comprises adding 4.6 g of citric acid to the mixture, and stirring the mixture until the citric acid is completed dissolved. Then, the method comprises adding 0.1 ml of Triton X-100 to the mixture, and stirring the mixture until the Triton X-100 is completed dissolved. Next, the method comprises adding more distilled water until the composition has a final volume of 100 ml. In one embodiment, the composition according to the present invention is dispensed into a container, the container is sealed, and the sealed container is stored until use.

According to another embodiment of the present invention, there is provided a method for reducing bacterial biofilm formation in connection with a dental procedure, where the method comprises providing a composition according to the present invention. In one embodiment, the dental procedure is selected from the group consisting of an endodontic procedure such as a root canal, preparation for placement of a restorative material, and preparation for placement of a dental crown. The method comprises providing a composition according to the present invention. In one embodiment, the method comprises, identifying a patient with a tooth that needs endodontic therapy. Then, the endodontic therapy is performed, such as for example removing some or all of the pulp of the tooth in the process of removing an infection. Next, the root canal is conventionally cleaned and shaped as well as filled following the obturation technique. After cleaning and shaping are done, and immediately before filling the root canal, the root canal system is irrigated with 5 ml per root canal with a composition according to the present invention, and the composition is allowed to contact the root canal system for a minimum of two minutes, and preferably for at least five minutes. In another embodiment, the method comprises, identifying a patient with a tooth that needs a dental procedure, such as for example a patient with a cavity prepared for placing a filing of a suitable material, such as for example amalgam, dental composites, glass ionomer cement, gold, or porcelain. Once the cavity has been prepared and is ready to be filled, the cavity is irrigated under isolation (rubber dam and clamp) with 3 ml of the composition according to the present invention, and the composition is allowed to contact the cavity for between one and two minutes. In a preferred embodiment, the cavity is then irrigated with an additional 2 ml of the composition. Then, the cavity is filled according to standard techniques. In another embodiment, the method comprises, identifying a patient with a tooth that needs a dental procedure, such as for example a patient prepared for placement of a dental crown. Next, the prepared tooth cavity is irrigated under isolation (rubber dam and clamp, or using high speed suction) with 3 ml of the composition according to the present invention, and the composition is allowed to contact the cavity and dry. In a preferred embodiment, the cavity is then irrigated with an additional 2 ml of the composition.

The effectiveness of a composition according to the present invention in reducing bacterial biofilm formation was demonstrated as follows. First, a microbial consortium was created using bacterial strains, *E. faecalis, L. salivarius* and *S. gordonii* which were isolated from endodontic therapy associated with persistent infections. The strains were stored at −70° C. using skim milk powder (Oxoid, Cambridge, United Kingdom), diluted in double distilled water and were recovered on blood agar in an atmosphere of 5% $CO_2$ in hydrogen at 37° C. for 24 hours. Then, four to five colonies of each strain were transferred into liquid growth medium (Todd-Hewitt broth) and incubated in an atmosphere of 5% $CO_2$ in hydrogen at 37° C. The optical densities (OD600) of the liquid cultures were monitored until exponential growth was reached, that is, until OD600 values of 0.6±0.1. The cells were harvested by centrifugation (3000 g, five minutes at 4° C.), washed in 10 mM PBS and re-suspended in Todd-Hewitt broth to an approximate cell concentration of $1\times10^8$ $ml^{-1}$. The inoculum for the microbial consortium was prepared by transferring 500 µl aliquots of each strain into 1.5 ml fresh Todd-Hewitt broth.

Next, biofilms were created in the mini-flow chamber system µ-Slide VI for Live Cell Analysis (Integrated BioDiagnostics, Munich, Germany) using techniques known to those with skill in the art. Briefly, each mini-flow chamber was inoculated with 30 µl of a washed suspension of cells grown to the mid-exponential phase in Todd-Hewitt broth, followed by addition of 100 µl of fresh Todd-Hewitt broth to give a final volume of 130 µl per mini-flow chamber. Prior to bacterial inoculation, selected channels were preconditioned in situ for 1 hour with a solution of benzalkonium chloride. A composition according to the present invention and a solution of 1% NaOCl were used as test compositions. The mini-flow chambers were incubated in an atmosphere of 5% $CO_2$ in hydrogen at 37° C., and adhesion was allowed to take place for 1, 6 and 24 hours under static conditions. After each time point and prior to microscopic analysis, chambers were rinsed with phosphate buffered saline to remove non-adherent cells.

Then, the mini-flow chamber biofilms were inspected. For the microscopic inspection of biofilm formation on plastic surfaces, the LIVE/DEAD BacLight Bacterial Viability kit (Invitrogen Corporation, Carlsbad, Calif., US) was used together with confocal scanning laser microscopy (CSLM). The LIVE/DEAD mixture was prepared and added to the mini-flow chambers according to techniques known to those with skill in the art. The microscope used was an inverted confocal scanning laser microscope (Eclipse TE2000, Nikon Inc., Melville, N.Y., US). Twenty randomly selected biofilm sections were imaged in three-dimensional stacks from each mini-flow chamber. 3-D stacks were composed of ten images, each taken with a variation of 2 µm along the z-position. Images were acquired with settings in the microscope according to techniques known to those with skill in the art. CSLM images were analyzed in 2 and 3-D by using the software bioImage_L. The overall volume of the biofilm including an estimate of the biomass and the percentage of substratum covered by biofilm cells were the main parameters used to analyze biofilm adhesion in mini-flow-chambers. Biofilm sections were reconstructed in 3-dimensions with the function 'structure and distribution' in the software bioImage_L.

The infected dentin disc model used in this demonstration was obtained from freshly extracted bovine incisors and were kept in 0.5% NaOCl overnight for surface disinfection. To standardize the size of the test specimens, dentin discs were prepared from the bovine teeth by removing the crown 3 mm apical to the cementoenamel junction by using a diamond disk rotating at 700 rpm under water cooling. The dentin discs were prepared under a water-cooled #2 trephine bur (Hu-Friedy International, Chicago, Ill., US). The dentin discs were smoothed with a diamond bur (Diamond 831L, Peter Brasseler Holdings, LLC, Savannah, Ga., US). Then, the dentin discs were maintained in tap water during all procedures to prevent dehydration. The smear layer was removed by treatment in an ultrasonic bath with 17% EDTA for four minutes followed by soaking in 5.25% NaOCl for four minutes. The discs were then autoclaved in water for twenty minutes at 121° C.

Each of the dentin discs were placed in a receptacle containing either 2 ml of the composition according to the present invention, or 2 ml of NaOCl solutions for one minute. Each dentin disc was then inoculated with bacteria from saliva. Then, each dentin disc was placed in 2 ml Trypticase Soy Broth for 4 days. The broth was replaced every 24 hours. Next, each disc was incubated for 48 hours at 37° C. and was checked for bacterial growth or turbidity.

Following incubation, each disc was placed in a 0.5 ml microtube (Excel Scientific, Inc., Victorville, Calif., US) containing 0.4 ml of phosphate buffered saline (PBS) and vortexed for 20 seconds. After the 4 days of incubation, each disc was processed with serial dilutions of alcohol and coated with platinum/palladium. Images of each dentin disc were taken with a scanning electron microscope (Philips XL30 ESEM) at 5000× magnification to evaluate the presence of bacteria on the dentin disc surface.

Bacterial growth was determined as follows. Each sample was placed in a tube of 2 ml BHI broth and incubated for 72 hours. An absence of turbidity demonstrated no bacterial growth, whereas turbidity demonstrated remaining viable bacteria. All samples were visually examined by two examiners to determine turbidity. All non-turbid test samples were vortexed and plated 25 ml onto BHI plates. Three positive and three negative control specimens were also plated on BHI plates. The plates were incubated for 24 hours and visually examined for the presence or absence of bacterial growth. Presence of growth was confirmed by visualization of individual white pinpoint colonies on the agar plates. Referring now to FIG. 1, there is shown a photograph of an agar plate processed in this manner where the test sample was treated with a composition according to the present invention. As can be seen, no bacterial growth is visible.

Each experiment was repeated three times and the statistical analysis was performed by two-way analysis of variance (ANOVA). Two-way ANOVA detected any significant variation among biofilms formed on surfaces pre-conditioned with the composition according to the present invention, NaOCl and the uncoated controls. Analysis for random variation (error) was also included.

Figure 2:
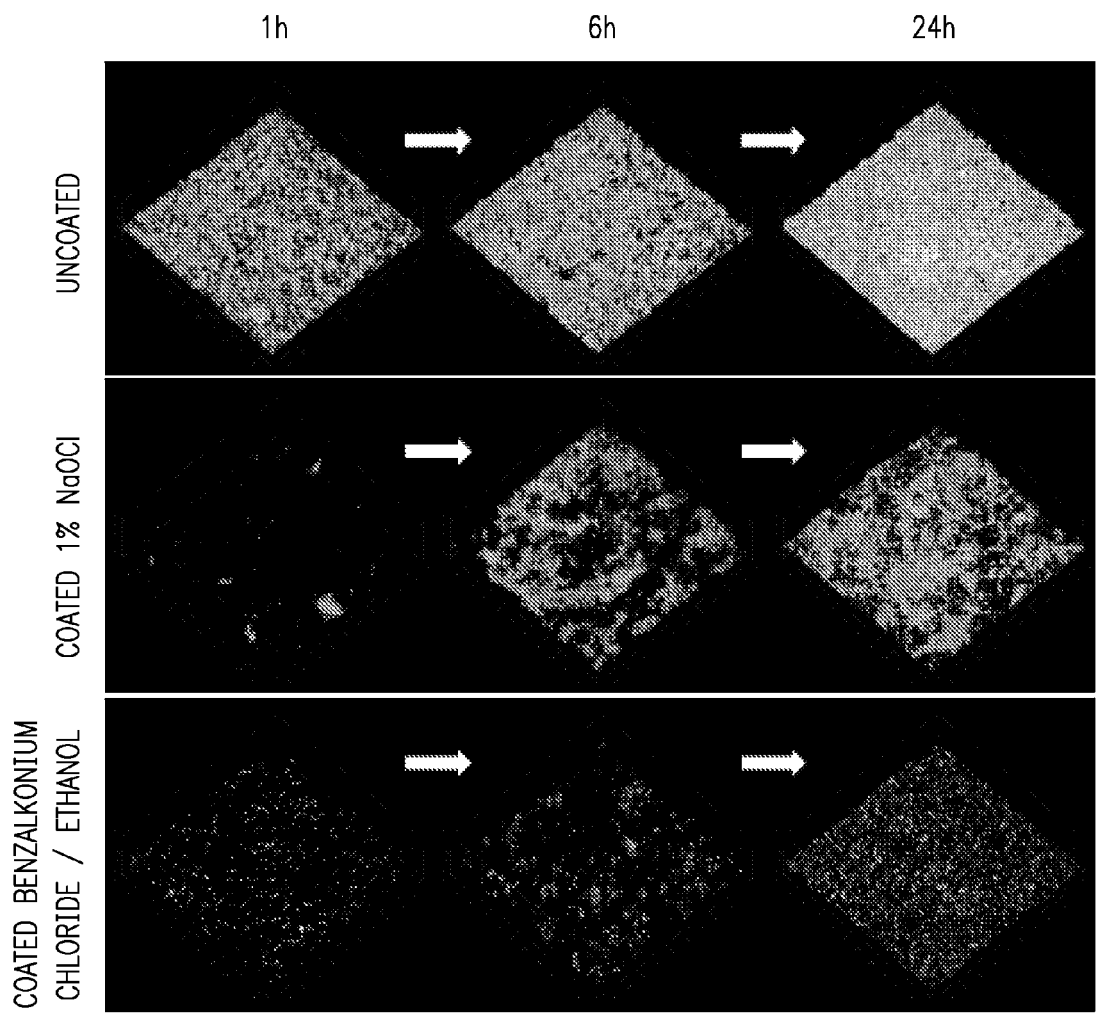
FIG. 2 is a 3-dimensional volume reconstruction of the biofilm sections comparing the uncoated controls (top), with pre-conditioning with NaOCl (middle) and with a composition according to the present invention (bottom)
Figure 3:
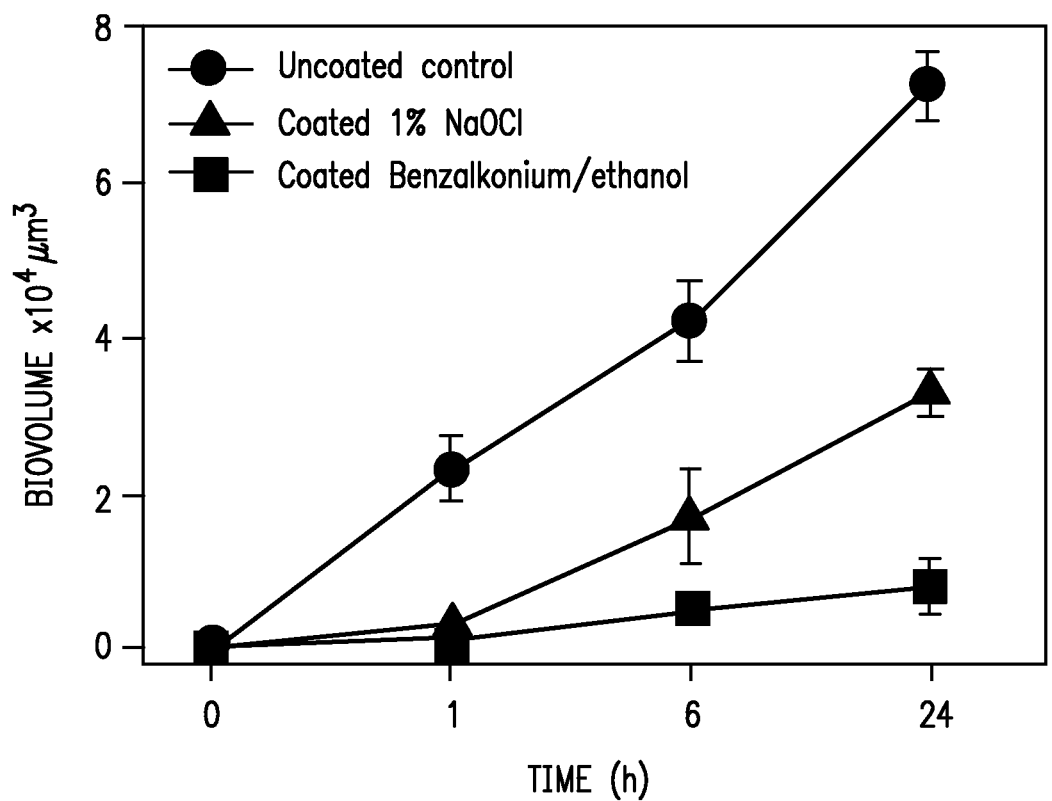
FIG. 3 is a graph plotting biovolume on the y axis and time on the x axis.

To characterize the biofilm-reducing potential of a composition according to the present invention, and to compare the potential with that of NaOCl, a mixed culture consortium of three root canal isolates, *E. faecalis, L. salivarius* and *S. gordonii*, was studied during biofilm growth in a mini-flow cell system. The mini-flow cell chambers were pre-conditioned with a composition according to the present invention or NaOCl and subsequently inoculated. The biofilms were then allowed to develop for 1, 6 and 24 hours. Referring now to FIG. 2, there is shown 3-dimensional volume reconstructions of the biofilm sections comparing the uncoated controls (top), with pre-conditioning with NaOCl (middle) and with a composition according to the present invention (bottom). As can be seen, the preconditioning of the mini-flow-chambers with a composition according to the present invention significantly reduced biofilm formation by the bacteria consortium compared to that on the uncoated controls. Referring now to FIG. 3, there is shown a graph plotting biovolum×$10^4$ in $\mu m^3$ on the y axis and time in hours on the x axis. As can be seen, at 1 hour of incubation the mass volume of biofilms formed on surfaces preconditioned with a composition according to the present invention was of $0.1\pm0.05\times10^4$ $\mu m^3$, while biofilms formed on the uncoated controls showed biovolumes that were 23-fold greater. At the following time points, 6 and 24 hours, the biovolume of biofilms formed on surfaces preconditioned with a composition according to the present invention remained sparse whereas biofilms formed on the uncoated controls showed biovolumes that were 70-fold greater. The biovolume of biofilms formed on surfaces preconditioned with NaOCl were intermediate between the biovolume of biofilms formed on surfaces preconditioned with a composition according to the present invention and the biovolume of biofilms formed on uncoated controls. In all tests, the viability of biofilm cells was not compromised as shown by the proportions of green-viable cells according to the LIVE/DEAD staining (FIG. 2). These findings indicate that the repelling effects of the composition according to the present invention and NaOCl were not linked to any cell membrane damage but rather on interfering with adhesion of cells to the pre-conditioned surfaces.

Figure 4:
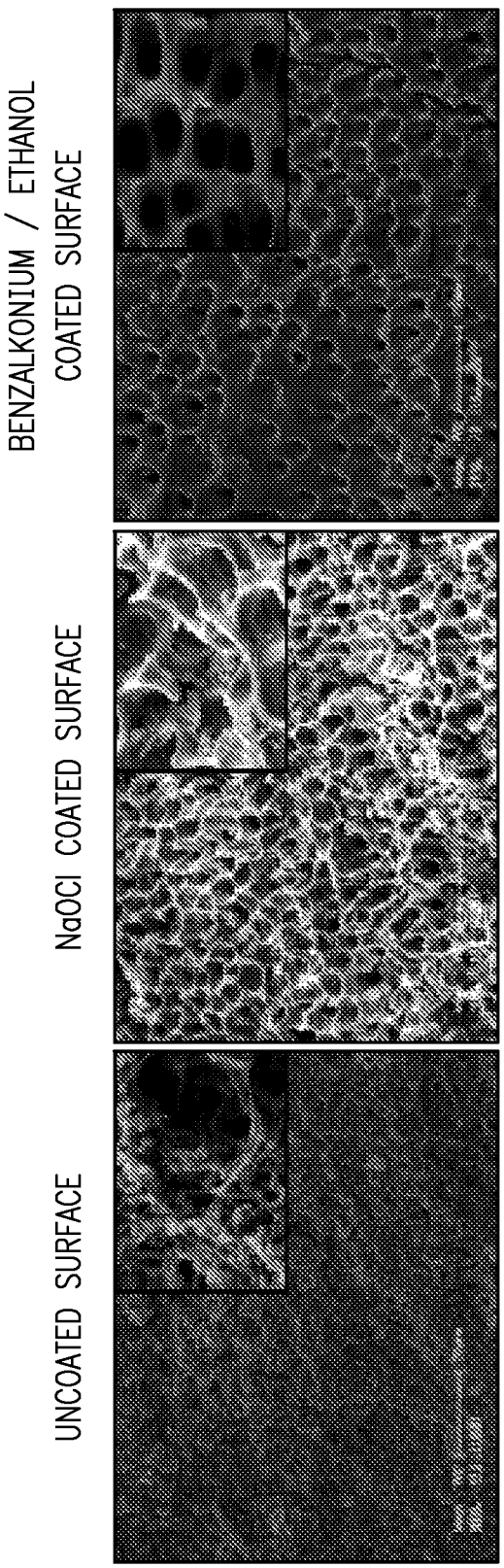
FIG. 4 are scanning electron microscope images of example surfaces that were uncoated (left), preconditioned with NaOCl (middle) and preconditioned with a composition according to the present invention (right).

Referring now to FIG. 4, there are shown scanning electron microscope images of example surfaces that were uncoated (left), preconditioned with NaOCl (middle) and preconditioned with a composition according to the present invention (right). As can be seen, the pre-conditioning of bovine dentine surfaces with a composition according to the present invention and with NaOCl significantly reduced biofilm formation. In the uncoated controls the mixed consortium of organisms formed layers of cells stacked on top of each other completely covering the entrance of dentinal tubules, whereas on pre-conditioned dentine surfaces the mixed culture did not form these tight structures keeping the lumen of dentinal tubules in most cases free of organisms.

Although the present invention has been discussed in considerable detail with reference to certain preferred embodiments, other embodiments are possible. Therefore, the scope of the appended claims should not be limited to the description of preferred embodiments contained in this disclosure. All references cited herein are incorporated by reference to their entirety.

The invention claimed is:

1. A composition for reducing bacterial biofilm formation in connection with a dental procedure, the composition comprising:
   a) about 60% by weight water;
   b) about 20% by weight ethanol;
   c) about 12% by weight benzalkonium chloride;
   d) about 5% by weight citric acid; and
   e) about 0.1% by weight of a nonionic surfactant.

2. A method for reducing bacterial biofilm formation in connection with a dental procedure, where the method comprises contacting a dental tissue with a composition according to claim 1.

3. The method of claim 2, where the dental procedure is selected from the group consisting of an endodontic procedure, preparation for placement of a restorative material, and preparation for placement of a dental crown.

4. A composition for reducing bacterial biofilm formation in connection with a dental procedure, the composition consisting essentially of:
   a) about 60% by weight water;
   b) about 20% by weight ethanol;
   c) about 12% by weight benzalkonium chloride;
   d) about 5% by weight citric acid; and
   e) about 0.1% by weight of a nonionic surfactant.

5. A method for reducing bacterial biofilm formation in connection with a dental procedure, where the method comprises contacting a dental tissue with a composition according to claim 4.

6. The method of claim 5, where the dental procedure is selected from the group consisting of an endodontic procedure, preparation for placement of a restorative material, and preparation for placement of a dental crown.

7. A composition for reducing bacterial biofilm formation in connection with a dental procedure, the composition comprising:
   a) 50-67% by weight water;
   b) 17.5-30% by weight ethanol;
   c) 11-14% by weight benzalkonium chloride;
   d) 4-5% by weight citric acid; and
   e) 0.09-0.11% by weight of a nonionic surfactant.

8. The composition of claim 7, where the water is distilled water.

9. The composition of claim 7, where the 50-67% water is about 60% water.

10. The composition of claim 7, where the 17.5-30% ethanol is about 20% ethanol.

11. The composition of claim 7, where the 11-14% benzalkonium chloride is about 12% benzalkonium chloride.

12. The composition of claim 7, where the 4-5% citric acid is about 5% citric acid.

13. The composition of claim 7, where the 0.09-0.11% nonionic surfactant is about 0.1% nonionic surfactant.

14. A method for reducing bacterial biofilm formation in connection with a dental procedure, where the method comprises contacting a dental tissue with a composition according to claim 7.

15. The method of claim 14, where the dental procedure is selected from the group consisting of an endodontic procedure, preparation for placement of a restorative material, and preparation for placement of a dental crown.

16. A composition for reducing bacterial biofilm formation in connection with a dental procedure, the composition consisting essentially of:
   a) 50-67% by weight water;
   b) 17.5-30% by weight ethanol;
   c) 11-14% by weight benzalkonium chloride;
   d) 4-5% by weight citric acid; and
   e) 0.09-0.11% by weight of a nonionic surfactant.

17. A composition for reducing bacterial biofilm formation in connection with a dental procedure, the composition comprising:
   a) 50-67% by weight of a water;
   b) 17.5-30% by weight of an alcohol;
   c) 11-14% by weight of a biocide;
   d) 4-5% by weight of a chelating agent; and
   e) 0.09-0.11% by weight of a surfactant.

18. The composition of claim 17, where the water is distilled water.

19. The composition of claim 17, where the alcohol is ethanol.

20. The composition of claim 17, where the biocide is benzalkonium chloride.

21. The composition of claim 17, where the chelating agent is citric acid.

22. The composition of claim 17, where the surfactant is a nonionic surfactant.

23. A method for reducing bacterial biofilm formation in connection with a dental procedure, where the method comprises contacting a dental tissue with a composition according to claim 17.

24. The method of claim 23, where the dental procedure is selected from the group consisting of an endodontic procedure, preparation for placement of a restorative material, and preparation for placement of a dental crown.

\* \* \* \* \*